(12) United States Patent
Cohen

(10) Patent No.: US 10,307,216 B2
(45) Date of Patent: Jun. 4, 2019

(54) BACKLIT SURGICAL INSTRUMENT SUPPORT ASSEMBLY

(71) Applicant: Ben Z. Cohen, New York, NY (US)

(72) Inventor: Ben Z. Cohen, New York, NY (US)

( * ) Notice: Subject to any disclaimer, the term of this patent is extended or adjusted under 35 U.S.C. 154(b) by 500 days.

(21) Appl. No.: 14/381,620

(22) PCT Filed: Feb. 28, 2013

(86) PCT No.: PCT/US2013/028161
§ 371 (c)(1),
(2) Date: Aug. 28, 2014

(87) PCT Pub. No.: WO2013/130710
PCT Pub. Date: Sep. 6, 2013

(65) Prior Publication Data
US 2015/0031960 A1    Jan. 29, 2015

Related U.S. Application Data

(60) Provisional application No. 61/604,161, filed on Feb. 28, 2012.

(51) Int. Cl.
*A61B 17/00* (2006.01)
*A61B 50/15* (2016.01)
(Continued)

(52) U.S. Cl.
CPC ............ *A61B 50/15* (2016.02); *A61B 46/00* (2016.02); *A61B 46/10* (2016.02); *A61B 50/10* (2016.02);
(Continued)

(58) Field of Classification Search
CPC ......... A61B 50/10; A61B 50/13; A61B 50/15; A61B 50/30; A61B 50/33; A61B 50/34;
(Continued)

(56) References Cited

U.S. PATENT DOCUMENTS 2,215,462 A    8/1940  Davidson, Jr. et al.
4,404,619 A *  9/1983  Ferguson ............ F21V 33/0012
                                                362/222
(Continued)

FOREIGN PATENT DOCUMENTS

WO    2004088463 A2    10/2004

OTHER PUBLICATIONS

San Diego Plastics Inc., "Polyurethane", http://www.sdplastics.com/polyuret.html, accessed Apr. 18, 2017.*
(Continued)

*Primary Examiner* — Matthew J Lawson
*Assistant Examiner* — Amy R Sipp
(74) *Attorney, Agent, or Firm* — Budzyn IP Law, LLC

(57) ABSTRACT

The subject invention provides a surgical instrument support assembly which includes an enclosure defining an opening; a light transmissive pane located at least partially across the opening and defining a support surface; and, a light source located inside the enclosure for generating light to be transmitted through the light transmissive pane. A sterilizable light transmissive surgical instrument support may be also provided to be disposed over at least a portion of the light transmissive pane. Advantageously, with the subject invention, an assembly is provided which includes a sterilized surface for supporting surgical instruments which is backlit. With this arrangement, surgical instruments may be supported and illuminated from beneath to aid a medical practitioner in identifying the surgical instruments.

5 Claims, 2 Drawing Sheets

(51) Int. Cl.
    *A61B 90/00*         (2016.01)
    *A61B 90/30*         (2016.01)
    *A61B 50/10*         (2016.01)
    *A61B 50/13*         (2016.01)
    *A61B 50/33*         (2016.01)
    *A61B 46/00*         (2016.01)
    *A61B 46/10*         (2016.01)
    *A61B 90/90*         (2016.01)
    *A61B 90/92*         (2016.01)
    *A61B 50/30*         (2016.01)

(52) U.S. Cl.
    CPC .............. *A61B 50/13* (2016.02); *A61B 50/33* (2016.02); *A61B 90/30* (2016.02); *A61B 90/36* (2016.02); *A61B 90/90* (2016.02); *A61B 90/92* (2016.02); *A61B 2050/105* (2016.02); *A61B 2050/155* (2016.02); *A61B 2050/3015* (2016.02)

(58) Field of Classification Search
    CPC ........ A61B 2050/105; A61B 2050/155; A61B 90/36; A61B 90/90; A61B 90/92; A61B 19/0271; F21V 33/0068
    USPC .......... 600/249; 362/33, 97.4, 133, 134, 127
    See application file for complete search history.

(56) References Cited

U.S. PATENT DOCUMENTS

| | | | |
|---|---|---|---|
| 4,927,214 A | | 5/1990 | Kaufman et al. |
| 5,170,804 A | | 12/1992 | Glassman |
| 5,605,393 A | * | 2/1997 | Cucchi ..................... A61D 3/00 108/23 |
| 5,607,737 A | * | 3/1997 | Blackwell .............. B42D 5/005 206/220 |
| 8,074,815 B2 | | 12/2011 | Gerstner |
| 2004/0208780 A1 | * | 10/2004 | Faries, Jr. ............. A61F 7/0085 422/3 |
| 2004/0264160 A1 | * | 12/2004 | Bienick .................. A47B 97/00 362/602 |
| 2005/0157505 A1 | * | 7/2005 | Dow ....................... A47B 13/12 362/374 |
| 2005/0212239 A1 | | 9/2005 | Carter |
| 2005/0226762 A1 | | 10/2005 | Naarup |
| 2006/0104856 A1 | | 5/2006 | Farrell et al. |
| 2010/0091482 A1 | * | 4/2010 | Dow ........................ F21S 8/00 362/127 |
| 2010/0158751 A1 | | 6/2010 | Friderich et al. |
| 2010/0200561 A1 | | 8/2010 | Faries, Jr. et al. |
| 2010/0259148 A1 | * | 10/2010 | Alberghetti ......... F21V 33/0012 312/408 |
| 2010/0266445 A1 | | 10/2010 | Campagna |

OTHER PUBLICATIONS

ROHM Semiconductor, "High-heat resistance, High-power White LEDs—PSL01 Series", http://www.rohm.com/web/global/news-detail?news-title=high-heat-resistance-high-power-white-leds-psl01-series&defaultGroupId=false, accessed Apr. 18, 2017.*

* cited by examiner

BACKLIT SURGICAL INSTRUMENT SUPPORT ASSEMBLY

CROSS-REFERENCES TO RELATED APPLICATIONS

This application is a National Stage Application under 35 U.S.C. § 371 of PCT International Application No. PCT/US2013/028161, filed Feb. 28, 2013, which claims priority to U.S. Provisional Patent Application No. 61/604,161, filed Feb. 28, 2012, the entire contents of which are incorporated by reference herein.

FIELD OF THE INVENTION

This invention relates to surgical instrument support assemblies and, more particularly, surgical instrument support assemblies which include backlighting.

BACKGROUND OF THE INVENTION

Surgical instrument support assemblies are known in the prior art. These assemblies are used to support, in sterilized conditions, various surgical instruments during a procedure or operation. Many settings for such surgical procedures or operations may be purposefully dimly lit around the patient. As such, the surgical instrument tray or table may be also dimly lit. In this environment, medical professionals may have difficulty identifying proper instrumentation for use.

SUMMARY OF THE INVENTION

The subject invention provides a surgical instrument support assembly which includes an enclosure defining an opening; a light transmissive pane located at least partially across the opening and defining a support surface; and, a light source located inside the enclosure for generating light to be transmitted through the light transmissive pane. A sterilizable light transmissive surgical instrument support may be also provided to be disposed over at least a portion of the light transmissive pane. Advantageously, with the subject invention, an assembly is provided which includes a sterilized surface for supporting surgical instruments which is backlit. With this arrangement, surgical instruments may be supported and illuminated from beneath to aid a medical practitioner in identifying the surgical instruments.

These and other features of the invention will be better understood through a study of the following detailed description and accompanying drawings.

DETAILED DESCRIPTION OF THE INVENTION

Figure 1:
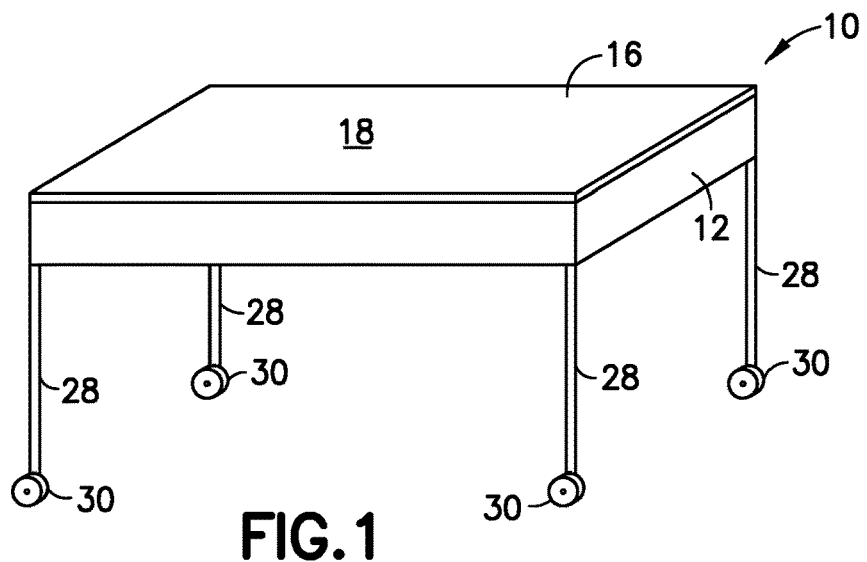
FIG. 1 is a perspective view of a surgical instrument support assembly formed in accordance with the subject invention in the form of a cart.

With reference to the Figures, a surgical instrument support assembly is shown and generally designated with the reference numeral 10. The surgical instrument support assembly 10 generally includes an enclosure 12, having an opening 14 defined therein; a light transmissive pane 16 located at least partially across the opening 14 and defining a support surface 18; and, one or more light sources 20 located inside the enclosure 12 configured to generate light to be transmitted through the light transmissive pane 16. The surgical instrument support assembly 10 advantageously may provide backlighting to a plurality of surgical instruments as further described below.

The enclosure 12 is a generally frame- or box-shaped construction which defines an interior volume 22 adjacent to the opening 14. The enclosure 12 also includes a plurality of sidewalls 24 which perimetrically bound the interior volume 22. The sidewalls 24 may be separate components which are fastened together or may be integrally formed together. The sidewalls 24 preferably are arranged in a rectangular configuration, but may be arranged to form other shapes such as a different polygonal shape, an ellipse, or an irregular shape. Preferably, a base 26 extends between the sidewalls 24 and encloses the interior volume 22 from the bottom.

Figure 2:
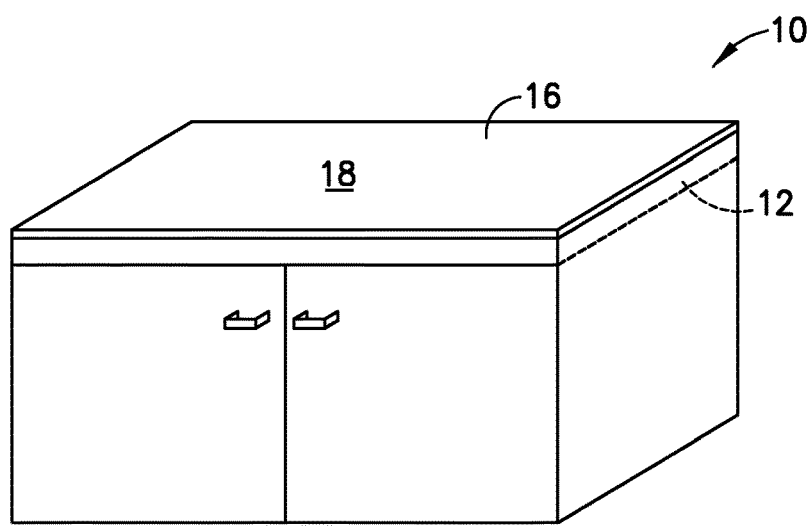
FIG. 2 is a perspective view of a surgical instrument support assembly formed in accordance with the subject invention in the form of a cabinet.
Figure 5:
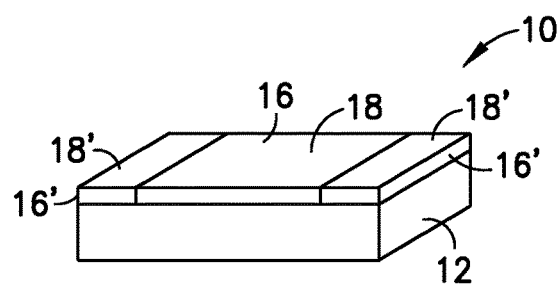

The enclosure 12 may be provided as part of a cart (FIG. 1), where one or more legs 28 may be provided to support the enclosure 12 with wheels 30 being optionally provided for permitting rolling movement of the enclosure 12. The legs 28 may be removably attachable to permit shipping or use of the enclosure 12 therewithout. Alternatively, the enclosure 12 may be formed as part of a cabinet or other article of furniture or equipment (FIG. 2), which may be stationary or moveable. Also, as shown in FIG. 5, the enclosure 12 may be a self-contained unit for mounting onto a cabinet, table or other support surface.

Preferably, the enclosure 12 is formed of robust construction and may be formed of thermoplastic and/or metallic material, such as stainless steel. Preferably, all joints and other points of connection defined on the enclosure 12 are provided to be liquid tight.

The opening 14 is defined with sufficiently large area so as to cover a suitable working area for supporting surgical instruments. The light transmissive pane 16 extends at least partially across the opening 14 and may completely span the opening 14. In this manner, as discussed below, light generated within the enclosure 12 may be transmitted through the light transmissive pane 16 via the opening 14. One or more additional panels 16' (FIG. 5) may be provided with the assembly 10 to cover portions of the opening 14 adjacent to the light transmissive pane 16. The one or more panels 16' may define one or more support surfaces 18' that are coextensive with the support surface 18.

The light transmissive pane 16 may be transparent or translucent. Preferably, the light transmissive pane 16 is light diffusive so as to diffuse light transmitted thereonto over an area of the light transmissive pane 16. Also, the light transmissive pane 16 may be formed of glass and/or polymeric material. It is preferred that the light transmissive pane 16 be fixed to the enclosure 12. Any mode of fixation known to those skilled in the art may be used including permanent or releasable fixation, e.g., snap-on or clamp-type fixation. With releasable fixation, the light transmissive pane 16 may be removable from the enclosure 12 so as to permit maintenance and sterilization of the light transmissive pane 16 separate from the enclosure 12. The panels 16' may be formed to be light transmissive or opaque.

The light sources 20 may be of any known type including being incandescent, LED, halogen and/or fluorescent. In addition, it is preferred that the light sources 20 generate white light, but other colors are also possible. Preferably, the light sources 20 include reflectors 32 for focusing generated light towards the light transmissive pane 16. The reflectors 32 need not be used, but this may result in less efficient operation of the assembly 10.

The light sources 20 are positioned within the enclosure 12 so as to provide a relatively even backlighting throughout all or a portion of the light transmissive pane 16. In addition, one or more controls 34 may be provided for permitting turning on/off the light sources 20 (e.g., switch 34A), and controlling the intensity of the light sources 20 (e.g., a dimmer 34B, which may be in the form of a rheostat). The controls 34 may be configured to permit control over individual units of the light sources 20, one or more subsets of the light sources 20, and/or control over all of the light sources 20 globally. The controls 34 may be configured to be controlled by various modes, such as, by voice control, hand control, foot pedals, and so forth.

Figure 3:
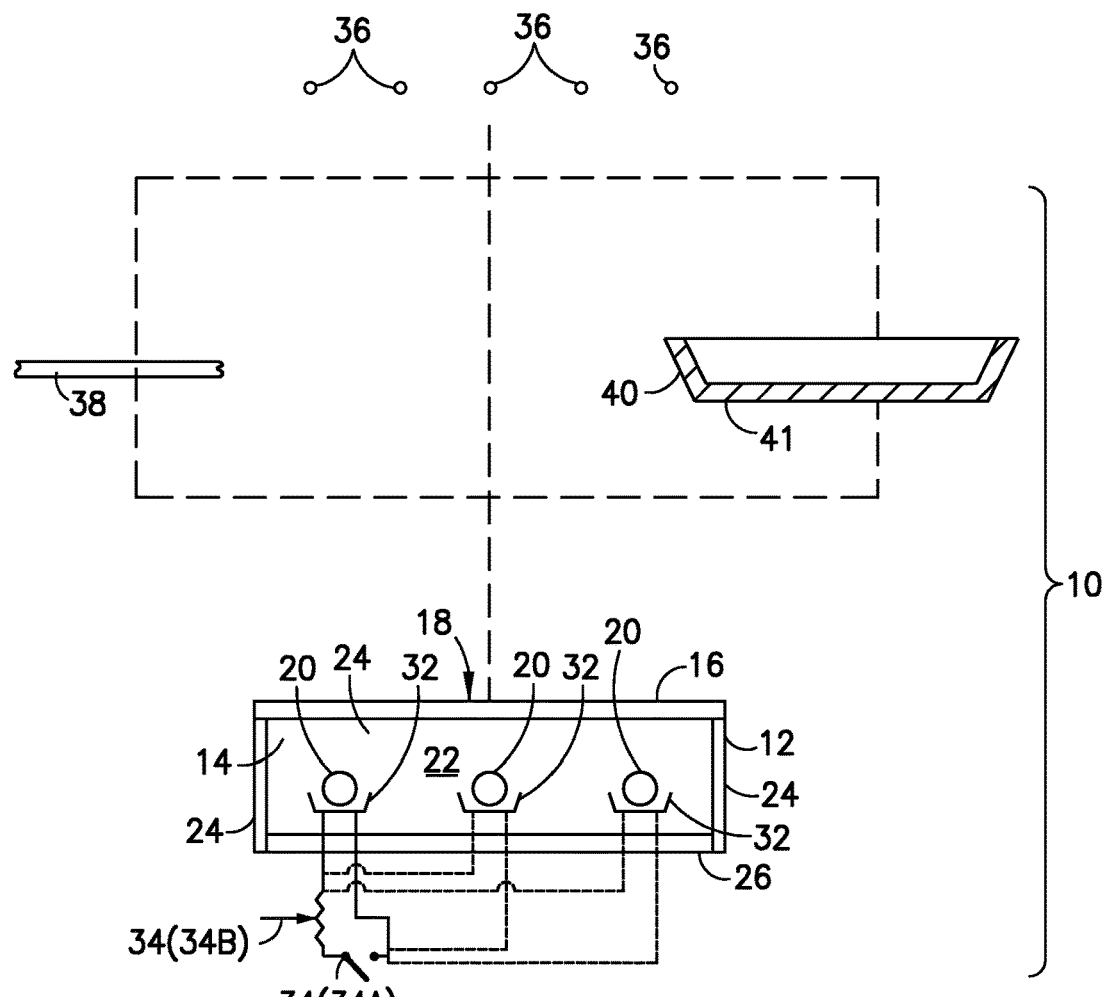
FIG. 3 is a schematic of a surgical instrument support assembly formed in accordance with the subject invention.

The surgical instrument support assembly 10 provides not only backlighting, but must also provide a sterile surface for supporting surgical instruments. With reference to FIG. 3, the support surfaces 18, 18' of the light transmissive pane 16 and the panels 16' may be sterilized, such as by chemical sterilization and/or other modes of sterilization. In consideration of the electrical components within the enclosure 12, the light transmissive pane 16 and the panels 16' may be formed to be removable from the enclosure 12 so as to permit sterilization of the light transmissive pane 16 and the panels 16', particularly the support surfaces 18, 18', separate from the enclosure 12 such as by known techniques, including, but not limited to, chemical cleaning, autoclaving, gamma radiation exposure, and/or exposure to ethylene oxide (EtO). Any known releaseable fasteners may be provided to permit releasable mounting of the light transmissive pane 16 and the panels 16' to the enclosure 12. In this manner, a plurality of surgical instruments 36 may be directly placed on the support surface 18 in a sterile state in preparation for a surgical procedure. Activation of the light sources 20 provides backlighting to the surgical instruments 36 atop the support surface 18 during a procedure. Contents of the enclosure 12, including the light sources 20, may be formed to be removable to permit sterilization of the enclosure 12. Known arrangements may be used to permit such removability.

In an alternative version, a sterile surgical instrument barrier may be placed atop the light transmissive pane 16 to support the surgical instruments 36. Here, sterilization of the light transmissive pane 16 may be avoided, depending on the circumstances. As shown in FIG. 3, sterile surgical drape 38 or sterile tray 40 may be provided to rest on the support surface 18 and to extend across at least a portion of the light transmissive pane 16. Portions of the surgical drape 38 and the tray 40 (such as all or part of bottom 41) are preferably formed to be light transmissive so as to permit transmission of light therethrough which radiates from the light transmissive pane 16. Transmission of light through the surgical drape 38 or the tray 40 provides backlighting to the surgical instruments 36.

Where the support surface 18 is to be utilized as the sterile support surface for the surgical instruments, the light transmissive pane 16 is preferably a seamless single pane having no internal seams. Alternatively, the light transmissive pane 16 may be formed by a plurality of joined sub-components; it is preferred that any seams formed between joined pieces be located outside of a target area for supporting the surgical instruments. If concerns exist over avoiding seams between components, the light transmissive pane 16 and the panels 16' may be fixed to the enclosure 12 within fixation configured to engage a bottom or side portion of the light transmissive pane 16 and the panels 16'—i.e., not the support surfaces 18, 18'—particularly where the support surfaces 18, 18' are utilized as a sterile support surface for the surgical instruments. For example, adhesive or mechanical fasteners may be used which engage the light transmissive pane 16 and the panels 16' below the support surfaces 18, 18'.

Figure 4:
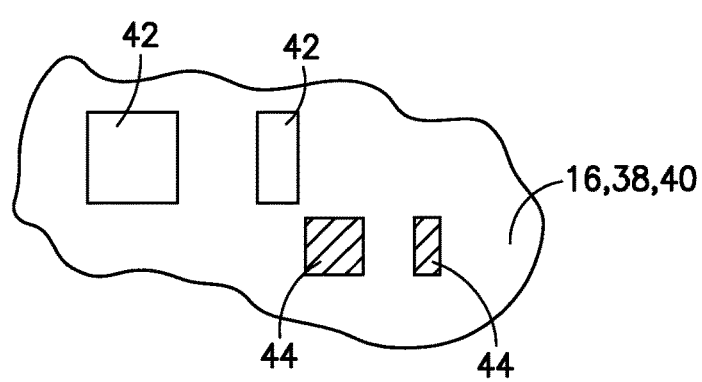
FIG. 4 is a top plan view of demarcated regions and areas of color for locating surgical instruments in accordance with the subject invention; and, FIG. 5 is a perspective view of a surgical instrument support assembly formed in accordance with the subject invention in the form of a self-contained unit for mounting onto a support surface.

As will be appreciated by those skilled in the art, certain portions of the light transmissive pane 16, the surgical drape 38, or the tray 40 may be demarcated by regions 42 and/or by areas of color 44, as shown in FIG. 4, with these regions or areas being light transmissive. With backlighting of the regions 42 or the areas of color 44, locations for particular surgical instruments, or groups of surgical instruments, may be designated. This not only assists in locating surgical instruments during a procedure but may also help in checking for a full complement of surgical instruments prior to a procedure.

What is claimed is:

1. A surgical instrument support assembly for supporting surgical instruments, the assembly comprising:
   an enclosure including a plurality of sidewalls perimetrically bounding an interior volume and a base enclosing a bottom of said interior volume, said enclosure defining an opening adjacent to said interior volume;
   a light transmissive pane located at least partially across said opening and defining a support surface;
   light means located inside said interior volume of said enclosure for generating light to be transmitted through said light transmissive pane, said light means being spaced from said light transmissive pane; and,
   a sterile light transmissive surgical instrument barrier including a surgical drape resting on, and disposed across, at least a portion of said light transmissive pane so as to define an exposed surface for supporting the surgical instruments, wherein portions of the surgical drape resting on said light transmissive pane including demarcated regions and/or areas of color to designate areas for one or more supported surgical instruments with said demarcated regions and/or areas of color being light transmissive, and, wherein the light generated by said light means transmits through said pane and said demarcated regions and/or areas of color to provide backlighting to any supported surgical instruments.

2. An assembly as in claim 1, further comprising means for adjusting the intensity of said generated light.

3. An assembly as in claim 1, wherein said support surface is seamless.

4. An assembly as in claim 1, wherein said support surface is sterilizable.

5. An assembly as in claim 1, wherein said light transmissive pane is releasably fixable to said enclosure.

* * * * *